(12) United States Patent
Marchueta Hereu et al.

(10) Patent No.: US 8,524,908 B2
(45) Date of Patent: Sep. 3, 2013

(54) PROCESS FOR MANUFACTURING 5-(2-{[6-(2,2-DIFLUORO-2-PHENYLETHOXY)HEXYL]AMINO}-1-HYDROXYETHYL)-8-HYDROXYQUINOLIN-2(1H)-ONE

(75) Inventors: Iolanda Marchueta Hereu, Barcelona (ES); Enrique Moyes Valls, Barcelona (ES)

(73) Assignee: Almirall, S.A., Barcelona (ES)

( * ) Notice: Subject to any disclaimer, the term of this patent is extended or adjusted under 35 U.S.C. 154(b) by 172 days.

(21) Appl. No.: 13/255,621

(22) PCT Filed: Mar. 12, 2010

(86) PCT No.: PCT/EP2010/001582
§ 371 (c)(1),
(2), (4) Date: Sep. 19, 2011

(87) PCT Pub. No.: WO2010/102831
PCT Pub. Date: Sep. 16, 2010

(65) Prior Publication Data
US 2012/0004414 A1 Jan. 5, 2012

(30) Foreign Application Priority Data
Mar. 12, 2009 (EP) ..................... 09382030

(51) Int. Cl.
C07D 215/38 (2006.01)

(52) U.S. Cl.
USPC ........................................ 546/157

(58) Field of Classification Search
USPC ........................................ 546/157
See application file for complete search history.

(56) References Cited

U.S. PATENT DOCUMENTS

| | | | |
|---|---|---|---|
| 2,579,479 A | 12/1951 | Djerassi et al. |
| 2,837,464 A | 6/1958 | Nobile |
| 2,897,216 A | 7/1959 | Oliveto et al. |
| 3,007,923 A | 11/1961 | Muller et al. |
| 3,053,865 A | 9/1962 | Taub et al. |
| 3,104,246 A | 9/1963 | Amiard et al. |
| 3,134,719 A | 5/1964 | Ranchhordas et al. |
| 3,678,137 A | 7/1972 | Pfeiffer et al. |
| 3,929,768 A | 12/1975 | Brattsand et al. |
| 3,970,677 A | 7/1976 | Nishimura et al. |
| 3,975,391 A | 8/1976 | Nakagawa et al. |
| 3,983,233 A | 9/1976 | Brattsand et al. |
| 3,994,901 A | 11/1976 | Nakagawa et al. |
| 4,022,776 A | 5/1977 | Nakagawa et al. |
| 4,022,784 A | 5/1977 | Nakagawa et al. |
| 4,026,897 A | 5/1977 | Nakagawa et al. |
| 4,068,076 A | 1/1978 | Nakagawa et al. |
| 4,145,542 A | 3/1979 | Nakagawa et al. |
| 4,753,962 A | 6/1988 | Ainsworth et al. |
| 4,992,474 A | 2/1991 | Skidmore et al. |
| 4,997,986 A | 3/1991 | Mitchell et al. |
| 5,099,068 A | 3/1992 | Mitchell et al. |
| 5,109,023 A | 4/1992 | Mitchell et al. |
| 5,201,308 A | 4/1993 | Newhouse |
| 5,263,475 A | 11/1993 | Altermatt et al. |
| 5,283,262 A | 2/1994 | Mitchell et al. |
| 5,435,301 A | 7/1995 | Herold et al. |
| 5,482,934 A | 1/1996 | Calatayud et al. |
| 5,507,281 A | 4/1996 | Kuhnel et al. |
| 5,617,845 A | 4/1997 | Poss et al. |
| 5,685,294 A | 11/1997 | Gupte et al. |
| 6,541,669 B1 | 4/2003 | Moran et al. |
| 7,498,321 B2 | 3/2009 | Biggadike et al. |
| 7,964,615 B2 * | 6/2011 | Puig Duran et al. ......... 514/312 |
| 8,178,679 B2 | 5/2012 | Matassa et al. |

(Continued)

FOREIGN PATENT DOCUMENTS

DE 2 236 272 2/1973
DE 2 323 215 11/1973

(Continued)

OTHER PUBLICATIONS

U.S. Appl. No. 11/920,561, filed Feb. 11, 2008, Puig Duran et al.
U.S. Appl. No. 12/298,131, filed Nov. 10, 2008, Puig Duran et al.
U.S. Appl. No. 12/444,935, filed May 14, 2009, Bach Taña et al.
U.S. Appl. No. 12/526,090, filed Oct. 8, 2009, Puig Duran et al.
U.S. Appl. No. 12/745,195, filed May 27, 2008, Giulio Matassa et al.
U.S. Appl. No. 12/919,134, filed Oct. 7, 2010, Puig Duran et al.
U.S. Appl. No. 13/094,156, filed Apr. 26, 2011, Puig Duran et al.

(Continued)

*Primary Examiner* — D M Seaman
(74) *Attorney, Agent, or Firm* — Finnegan, Henderson, Farabow, Garrett & Dunner, LLP

(57) ABSTRACT

A process for preparing a compound of formula (I), or a pharmaceutically acceptable salt thereof,

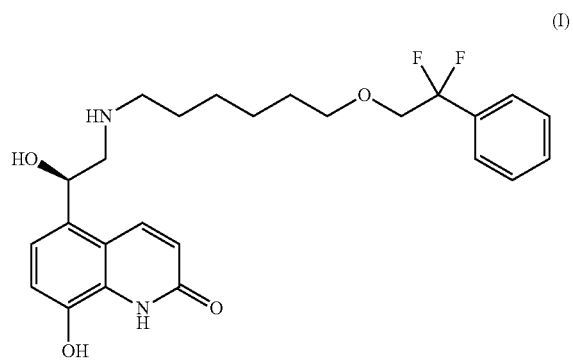

(I)

which process comprises:
a) reacting, in a xylene solvent, a compound of formula (V) having $P_1$ and $P_2$ protecting groups, with a compound of formula (IV), to give a compound of formula (III); and
b) effecting a $P_1$ deprotection step and a $P_2$ deprotection step to give a compound of formula (I); and optionally
c) preparing a pharmaceutically acceptable salt of a compound of formula (I);
wherein the compounds of formulas III, IV, and V are described in the specification.

16 Claims, 1 Drawing Sheet

(56) References Cited

U.S. PATENT DOCUMENTS

| | | | |
|---|---|---|---|
| 8,242,177 B2 | 8/2012 | Duran et al. | |
| 8,283,342 B2* | 10/2012 | Puig Duran et al. | 514/171 |
| 8,420,669 B2* | 4/2013 | Puig Duran et al. | 514/171 |
| 2002/0055651 A1 | 5/2002 | Moran et al. | |
| 2003/0136405 A1 | 7/2003 | Goede et al. | |
| 2003/0153597 A1 | 8/2003 | Moran et al. | |
| 2004/0059116 A1 | 3/2004 | Moran et al. | |
| 2004/0167167 A1 | 8/2004 | Mammen et al. | |
| 2005/0043337 A1 | 2/2005 | Rito et al. | |
| 2005/0159448 A1 | 7/2005 | McKinnell et al. | |
| 2005/0192316 A1 | 9/2005 | Moran et al. | |
| 2005/0215590 A1 | 9/2005 | Brown et al. | |
| 2005/0272769 A1 | 12/2005 | Linsell | |
| 2006/0019991 A1 | 1/2006 | McKinnell et al. | |
| 2006/0035931 A1 | 2/2006 | Chao et al. | |
| 2006/0081246 A1 | 4/2006 | Goede et al. | |
| 2006/0178410 A1 | 8/2006 | Moran et al. | |
| 2006/0205949 A1 | 9/2006 | Dalziel et al. | |
| 2007/0197536 A1 | 8/2007 | Dal Piaz et al. | |
| 2009/0042933 A1 | 2/2009 | Duran et al. | |
| 2009/0082378 A1 | 3/2009 | Puig Duran et al. | |
| 2010/0093681 A1 | 4/2010 | Puig Duran et al. | |
| 2010/0168161 A1 | 7/2010 | Taña et al. | |
| 2010/0324000 A1 | 12/2010 | Giulio Matassa et al. | |
| 2011/0028442 A1 | 2/2011 | Puig Duran et al. | |
| 2011/0251165 A1 | 10/2011 | Puig Duran et al. | |
| 2011/0251166 A1 | 10/2011 | Puig Duran et al. | |
| 2011/0251234 A1 | 10/2011 | Carrera Carrera et al. | |
| 2012/0029014 A1 | 2/2012 | Ruf et al. | |
| 2012/0040941 A1 | 2/2012 | Ruf et al. | |

FOREIGN PATENT DOCUMENTS

| | | |
|---|---|---|
| DE | 2 310 140 | 9/1974 |
| DE | 24 61 861 | 8/1975 |
| DE | 41 29 535 A1 | 3/1992 |
| DE | 42 39 402 A1 | 5/1994 |
| EP | 0 057 401 A1 | 8/1982 |
| EP | 0 069 715 A1 | 1/1983 |
| EP | 0 147 719 A2 | 7/1985 |
| EP | 0 166 294 A2 | 1/1986 |
| EP | 0 286 242 A2 | 10/1988 |
| EP | 0 317 206 A2 | 5/1989 |
| EP | 0 424 790 A2 | 5/1991 |
| EP | 0 505 321 A2 | 9/1992 |
| EP | 0 674 533 B1 | 3/1999 |
| EP | 1 078 629 A2 | 2/2001 |
| EP | 1 235 787 B1 | 10/2003 |
| EP | 1 577 291 A1 | 9/2005 |
| ES | 2 232 306 A1 | 5/2005 |
| GB | 0 869 511 | 5/1961 |
| GB | 1 200 886 | 8/1970 |
| GB | 1 247 370 | 9/1971 |
| GB | 1 458 251 | 12/1976 |
| GB | 1 468 156 | 3/1977 |
| GB | 2 041 763 A | 9/1980 |
| GB | 2 140 800 A | 12/1984 |
| GB | 2 160 863 A | 1/1986 |
| GB | 2 165 159 A | 4/1986 |
| GB | 2 242 134 A | 9/1991 |
| JP | 51-149282 A | 12/1976 |
| JP | 59-093051 A | 5/1984 |
| WO | WO 91/02558 A1 | 3/1991 |
| WO | WO 91/14468 A1 | 10/1991 |
| WO | WO 92/00771 A1 | 1/1992 |
| WO | WO 92/03175 A1 | 3/1992 |
| WO | WO 92/04068 A1 | 3/1992 |
| WO | WO 92/04928 A2 | 4/1992 |
| WO | WO 92/09322 A1 | 6/1992 |
| WO | WO 96/32150 A1 | 10/1996 |
| WO | WO 97/00703 A1 | 1/1997 |
| WO | WO 97/12687 A1 | 4/1997 |
| WO | WO 98/09632 A1 | 3/1998 |
| WO | WO 99/30703 A1 | 6/1999 |
| WO | WO 99/64035 A1 | 12/1999 |
| WO | WO 01/36375 A1 | 5/2001 |
| WO | WO 01/42193 A1 | 6/2001 |
| WO | WO 02/066422 A1 | 8/2002 |
| WO | WO 02/070490 A1 | 9/2002 |
| WO | WO 02/092606 A1 | 11/2002 |
| WO | WO 03/000325 A1 | 1/2003 |
| WO | WO 03/042160 A1 | 5/2003 |
| WO | WO 03/061742 A2 | 7/2003 |
| WO | WO 03/072539 A1 | 9/2003 |
| WO | WO 03/091204 A1 | 11/2003 |
| WO | WO 03/097613 A1 | 11/2003 |
| WO | WO 03/099764 A1 | 12/2003 |
| WO | WO 2004/011416 A1 | 2/2004 |
| WO | WO 2004/016578 A2 | 2/2004 |
| WO | WO 2004/058729 A1 | 7/2004 |
| WO | WO 2004/089892 A2 | 10/2004 |
| WO | WO 2004/106279 A2 | 12/2004 |
| WO | WO 2005/030678 A2 | 4/2005 |
| WO | WO 2005/049581 A1 | 6/2005 |
| WO | WO 2005/121065 A2 | 12/2005 |
| WO | WO 2005/123692 A1 | 12/2005 |
| WO | WO 2005/123693 A1 | 12/2005 |
| WO | WO 2006/023457 A1 | 3/2006 |
| WO | WO 2006/051375 A1 | 5/2006 |
| WO | WO 2006/122788 A1 | 11/2006 |
| WO | WO 2007/124898 A1 | 11/2007 |
| WO | WO 2008/046598 A1 | 4/2008 |
| WO | WO 2008/095720 A1 | 8/2008 |
| WO | WO 2009/068177 A1 | 6/2009 |
| WO | WO 2009/106351 A1 | 9/2009 |
| WO | WO 2010/072354 A1 | 7/2010 |
| WO | WO 2010/094483 A1 | 8/2010 |
| WO | WO 2010/094484 A1 | 8/2010 |
| WO | WO 2010/102831 A1 | 9/2010 |

OTHER PUBLICATIONS

U.S. Appl. No. 13/094,163, filed Apr. 26, 2011, Puig Duran et al.
U.S. Appl. No. 13/141,156, filed Jun. 21, 2011, Carrera Carrera et al.
U.S. Appl. No. 13/202,020, filed Oct. 18, 2011, Ruf et al.
U.S. Appl. No. 13/202,025, filed Oct. 14, 2011, Ruf et al.
U.S. Appl. No. 13/428,450, filed Mar. 23, 2012, Giulio Matassa et al.
U.S. Appl. No. 13/538,117, filed Jun. 29, 2012, Bach Taña et al.
Bastin, R.D. et al. "Salt Selection and Optimisation for Pharmaceutical New Chemical Entities," *Organic Process Research and Development*, 4(5):427-435 (2000).
Budesonide, Merck Index, Monograph No. 01468 (2012).
CAPLUS$^{SM}$ English Abstract of DE 2 236 272, Accession No. 1973:405128.
CAPLUS$^{SM}$ English Abstract of DE 2 310 140, Accession No. 1975:31115.
CAPLUS$^{SM}$ English Abstract of journal article by De Meglio, P. et al., Accession No. 1980:426036.
CAPLUS$^{SM}$ English Abstract of JP 51 149 282, Accession No. 1977:468184.
CAPLUS$^{SM}$ English Abstract of JP 59 093 051, Accession No. 1985:45790.
Ciclesonide, Merck Index, Monograph No. 02263 (2012).
Coleman, R.A. et al. "Novel and Versatile Superfusion System: Its Use in the Evolution of Some Spasmogenic and Spasmolytic Agents Using Guinea-pig Isolated Tracheal Smooth Muscle," *Journal of Pharmacological Methods*, 21:71-86 (1989).
Cortijo, J. et al. "Effects of dantrolene on the responses to methylxanthines in the isolated guinea-pig trachea," *European Journal of Pharmacology*, 198:171-176 (1991).
Curran, P.K. et al. "Endogenous $\beta_3$—But Not $\beta_1$-Adrenergic Receptors are Resistant to Agonist-Mediated Regulation in Human SK-N-MC Neurotumor Cells," *Cell. Signal.*, 8(5):355-364 (1996).
De Meglio, P. et al. "Synthesis and pharmacological study of orciprenaline and salbutamol derivatives," *Farmaco, Edizione Scientifica*, 35(3): 203-230 (1980).
Dexamethasone, Merck Index, Monograph No. 02943 (2011).
Deyrup, M.D. et al. "Structure-affinity profile of 8-hydroxycarbostyril-based agonists that dissociate slowly from the $\beta_2$-adrenoceptor," *Naunyn-Schmiedeberg's Archives of Pharmacology*, 359:168-177(1999).
DIALOG® File 349: PCT Fulltext, English Abstract of WO 2002/92606, Accession No. 00958733, 2 pp. (Nov. 21, 2002).

Furuie, H. et al. "Suppressive effect of novel phosphodiesterase4 (PDE4) inhibitor ONO-6126 on TNF-α release was increased after repeated oral administration in healthy Japanese subjects," 13th ERS Annual Congress, Sep. 27, 2003, Vienna. *Eur. Resp. Journal*, 22(Supp. 45):Abstract 2557 (2003).

Han "Advances in Characterization of Pharmaceutical Hydrates," *Trends in Bio/Pharmaceutical Industry*, 2(3):25-29 (2006).

Hart, D.J. "A Synthesis of (±)-Gephyrotoxin," *Journal of Organic Chemistry*, 46:3576-3578 (1981).

Hart, D.J. et al. "Total Syntheses of dl-Gephyrotoxin and dl-Dihydrogephyrotoxin," *J. Am. Chem. Soc.*, 105(5):1255-1263 (1983).

Hashima, H. et al. "Synthesis and Biological Activities of the Marine Byrozoan Alkaloids Convolutamines A, C and F, and Lutamides A and C," *Bioorganic & Medicinal Chemistry*, 8:1757-1766 (2000).

Hett, R. et al. "Enantioselective Synthesis of Salmeterol via Asymmetric Borane Reduction," *Tetrahedron Letters*, 35(50):9375-9378 (1994).

Hett, R. et al. "Large-Scale Synthesis of Enantio- and Diastereomerically Pure (R,R)-Formoterol," *Organic Process Research & Development*, 2(2):96-99 (1998).

International Search Report mailed Sep. 12, 2006, for International Application No. PCT/EP2006/004680 (WO 2006/122788 A1).

International Search Report mailed Apr. 21, 2009, for International Application No. PCT/EP2009/001431 (WO 2009/106351).

International Search Report mailed Jun. 21, 2007, for International Application No. PCT/EP2007/003601 (WO 2007/124898 A1).

International Search Report mailed Mar. 19, 2008, for International Application No. PCT/EP2007/008992 (WO 2008/046598 A1).

International Search Report mailed Mar. 2, 2010, for International Application No. PCT/EP2009/008970 (WO 2010/072354).

International Search Report mailed May 25, 2010, for International Application No. PCT/EP2010/001027 (WO 2010/094484).

International Search Report mailed May 27, 2010, for International Application No. PCT/EP2010/001026 (WO 2010/094483).

International Search Report mailed May 28, 2008, for International Application No. PCT/EP2008/000975 (WO 2008/095720).

International Search Report mailed May 7, 2009, for International Application No. PCT/EP2008/009469 (WO 2009/068177).

Ismail, F.M.D. "Important fluorinated drugs in experimental and clinical use," *Journal of Fluorine Chemistry* 118:27-33 (2002).

Johnson, M. "Salmeterol," *Medicinal Research Reviews*, 15(3):225-257 (1995).

Kaiser, C. et al. "Adrenergic Agents. 1. Synthesis and Potential β-Adrenergic Agonist Activity of Some Catecholamine Analogs Bearing a Substituted Amino Functionality in the Meta Position," *J. Med. Chem.*, 17(1):49-57 (1974).

Kikkawa, H. et al. "Differential contribution of two serine residues of wild type and constitutively active $β_2$-adrenoreceptors to the interaction with $β_2$-selective agonists," *British Journal of Pharmacology*, 121:1059-1064 (1997).

Meyers, A.I. et al. "Oxazolines. XI. Synthesis of Functionalized Aromatic and Aliphatic Acids. A Useful Protecting Group for Carboxylic Acids against Grignard and Hydride Reagents," *J. Org. Chem.*, 39(18): 2787-2793 (1974).

Meyers, A.I. et al. "Substitutions on 1-Methoxynaphthalenes via their Oxazoline Derivatives: A Convenient Route to 1-Substituted Naphthoic Acids," *Synthesis Communications*, 2:105-107 (1983).

Mometasone, Merck Index, Monograph No. 06241 (2012).

Morissette, S.L. et al. "High-Throughput Crystallization: Polymorphs, Salts, Co-Crystals and Solvates of Pharmaceutical Solids," *Advanced Drug Delivery Reviews*, 56:275-300 (2004).

Murase, K. et al. "New β-Adrenoreceptor Stimulants. Studies on 3-Acylamino-4-hydroxy-α-(N-substituted aminomethyl)benzyl Alcohols," *Chem. Pharm. Bull.*, 25(6):1368-1377 (1977).

Nielsen, K.G. et al. "Flow-dependent effect of formoterol dry-powder inhaled from the Aerolizer®," *Eur. Respir. J.*, 10:2105-2109 (1997).

Patani, G.A. et al. "Bioisosterism: A Rational Approach in Drug Design," *Chem. Rev.* 96:3147-3176 (1996).

Portoghese, P.S. "Stereochemical Studies on Medicinal Agents. 19. X-Ray Crystal Structures of Two (±)-Allylprodine Diastereomers. The Role of the Allyl Group in Conferring High Stereoselectivity and Potency at Analgetic Receptors," J. Med. Chem., 19(1):55-57 (1976).

Prednisone, Merck Index, Monograph No. 07722 (2012).

Silverman, R.B. *The Organic Chemistry of Drug Design and Drug Action*. Academic Press, Chapter 2, pp. 10-23 (1992).

Smart, B.E. "Fluorine substituent effects (on bioactivity)," *Journal of Fluorine Chemistry* 109:3-11 (2001).

Sterling, J. et al. "Novel Dual Inhibitors of AChE and MAO Derived from Hydroxy Aminoindan and Phenethylamine as Potential Treatment for Alzheimer's Disease," *J. Med. Chem.* 45(24):5260-5279 (2002).

STN Search Report, File CAPLUS, Accession No. 2003:875242, CAS RN 620599-83-9 (2011).

Svenson, R. et al. "On the Hydrozirconation of Some Long-Chain Unsaturated Fatty Acid Oxazolines," *Chemica Scripta.* 19:149-153 (1982).

Vippagunta, SR et al. "Crystalline Solids," *Advanced Drug Delivery Reviews* 48:3-26 (2001).

Williams, D.A. et al. (eds.) *FOYE's Principles of Medicinal Chemistry*. 5th Edition, Lippincott Williams & Wilkins, 2002; pp. 59-63.

Yang, Z. "Synthesis of new α,α,β,β-tetrafluoroesters," *Journal of Fluorine Chemistry* 125:763-765 (2004).

Yang, Z. et al. "A Novel and Practical Method for the Preparation of α,α-Difluoro Functionalized Esters," *J. Chem. Soc., Chem. Commun.* 3:233-234 (1992).

Yoshizaki, S. et al. "Sympathomimetic Amines Having a 3,4-Dihydrocarbostyril Nucleus," *Chemical and Pharmaceutical Bulletin* 26(5):1611-1614 (1978).

Yoshizaki, S. et al. "Sympathomimetic Amines Having a Carbostyril Nucleus," *J. Med. Chem.* 19(9):1138-1142 (1976).

U.S. Appl. No. 11/920,561: Restriction Requirement dated Mar. 16, 2010.

U.S. Appl. No. 11/920,561: Office Action dated Jun. 2, 2010.

U.S. Appl. No. 11/920,561: Interview Summary dated Jun. 11, 2010.

U.S. Appl. No. 11/920,561: Office Action (Quayle Action) dated Nov. 9, 2010.

U.S. Appl. No. 11/920,561: Notice of Allowance dated Jan. 26, 2011.

U.S. Appl. No. 12/298,131: Office Action dated Apr. 25, 2011.

U.S. Appl. No. 12/298,131: Office Action dated Jan. 26, 2012.

U.S. Appl. No. 12/444,935: Restriction Requirement dated May 13, 2011.

U.S. Patent Application No. 12/444,935: Office Action dated Jul. 7, 2011.

U.S. Appl. No. 12/444,935: Office Action dated Jan. 30, 2012.

U.S. Appl. No. 12/444,935: Office Action (Advisory Action) dated Jun. 4, 2012.

U.S. Appl. No. 12/526,090: Restriction Requirement dated Jul. 20, 2011.

U.S. Appl No. 12/526,090: Office Action dated Oct. 14, 2011.

U.S. Appl. No. 12/526,090: Office Action dated Apr. 24, 2012.

U.S. Appl. No. 12/526,090: Interview Summary dated Jun. 26, 2012.

U.S. Appl. No. 12/526,090: Notice of Allowance dated Jun. 26, 2012.

U.S. Appl. No. 12/745,195: Restriction Requirement dated Jan. 5, 2011.

U.S. Appl. No. 12/745,195: Office Action dated Mar. 9, 2011.

U.S. Appl. No. 12/745,195: Office Action dated Jul. 15, 2011.

U.S. Appl. No. 12/745,195: Notice of Allowance dated Dec. 28, 2011.

U.S. Appl. No. 12/745,195: Interview Summary dated Feb. 22, 2012.

U.S. Appl. No. 12/745,195: Notice of Allowance dated Feb. 24, 2012.

U.S. Appl. No. 13/094,156: Restriction Requirement dated Dec. 29, 2011.

U.S. Appl. No. 13/094,156: Office Action (Quayle Action) dated Feb. 14, 2012.

U.S. Appl. No. 13/094,156: Notice of Allowance dated Apr. 18, 2012.

U.S. Appl. No. 13/094,163: Restriction Requirement dated Jul. 6, 2012.

U.S. Appl. No. 13/094,163: Office Action dated Aug. 20, 2012.

U.S. Appl. No. 13/202,020: Restriction Requirement dated Oct. 2, 2012.
U.S. Appl. No. 13/202,025: Restriction Requirement dated Oct. 4, 2012.

International Search Report for International Application No. PCT/EP2010/001582 mailed Apr. 28, 2010.

* cited by examiner

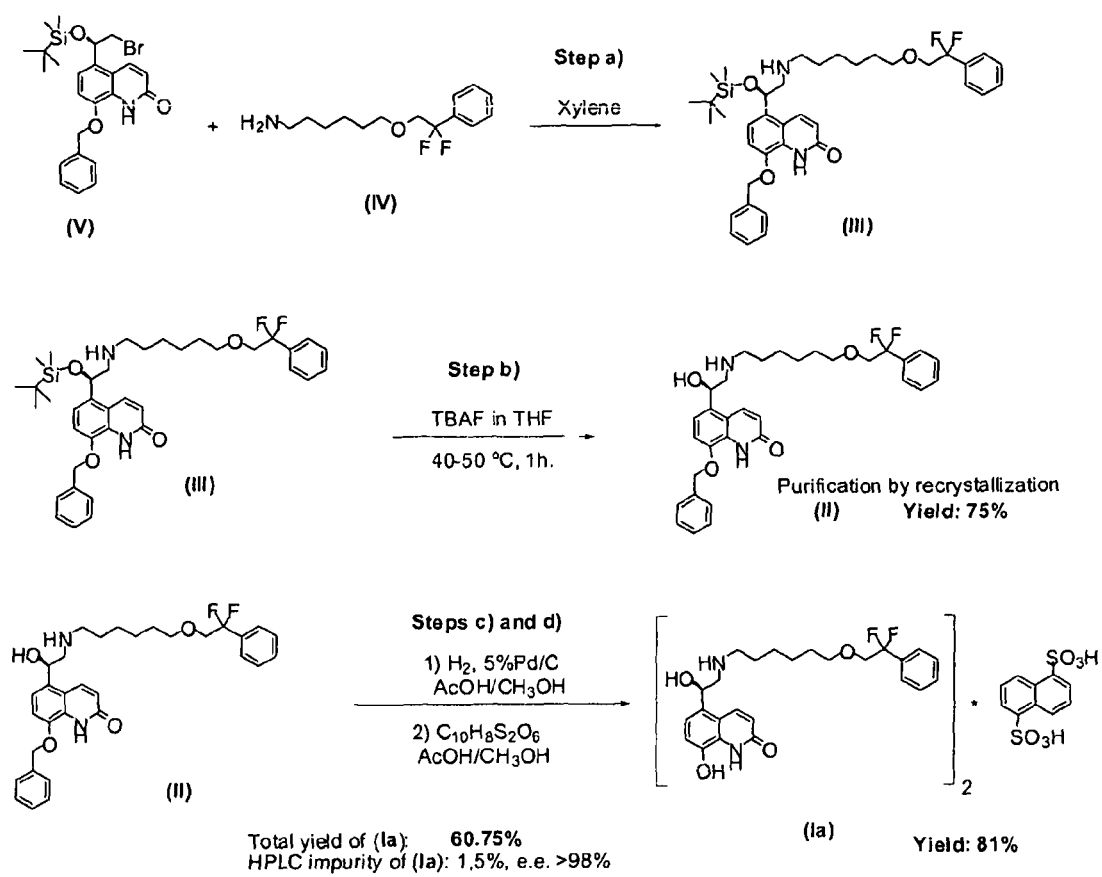

PROCESS FOR MANUFACTURING 5-(2-{[6-(2,2-DIFLUORO-2-PHENYLETHOXY)HEXYL]AMINO}-1-HYDROXYETHYL)-8-HYDROXYQUINOLIN-2(1H)-ONE

This application is a national stage entry under 35 U.S.C. §371 of International Application No. PCT/EP2010/001582 filed on Mar. 12, 2010, which claims priority of European Patent Application No. 09382030.6, filed on Mar. 12, 2009. The contents of both applications are incorporated herein by reference.

The present invention relates to an improved process for the manufacture of 5-(2-{[6-(2,2-difluoro-2-phenylethoxy)hexyl]amino}-1-hydroxyethyl)-8-hydroxyquinolin-2(1H)-one and pharmaceutically acceptable salts thereof.

5-(2-{[6-(2,2-difluoro-2-phenylethoxy)hexyl]amino}-1-hydroxyethyl)-8-hydroxyquinolin-2(1H)-one (compound (I)) as well as a process for its manufacture are described in WO 2006122788 A1.

Napadisylate salt of 5-(2-{[6-(2,2-difluoro-2-phenylethoxy)hexyl]amino}-1-hydroxyethyl)-8-hydroxyquinolin-2(1H)-one as well as a process for its manufacture are described in WO 2008095720 A1.

The inventors have now unexpectedly found that it is possible to (a) increase the yield of compound (I) and its salts, (b) minimise the amount of impurities in the final product and/or (c) decrease the reaction time, by modifying the synthetic processes described in WO 2006122788 A1 and WO 2008095720 A1.

These objectives can be achieved by selecting specific solvents and/or modifying or even removing some purification steps, thus reducing the reaction time while increasing the overall yield of the final product. Moreover, the process of the present invention is more suitable for large scale manufacture.

WO 2006122788 A1 describes a three step process for the preparation of 5-(2-{[6-(2,2-difluoro-2-phenylethoxy)hexyl]amino}-1-hydroxyethyl)-8-hydroxyquinolin-2(1H)-one Step a)

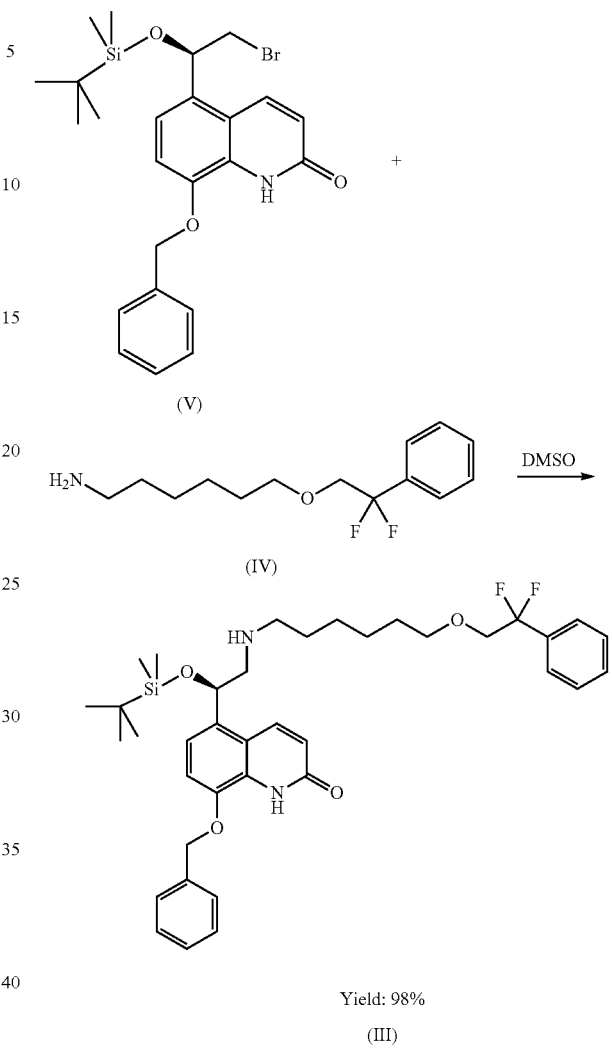

Step b)

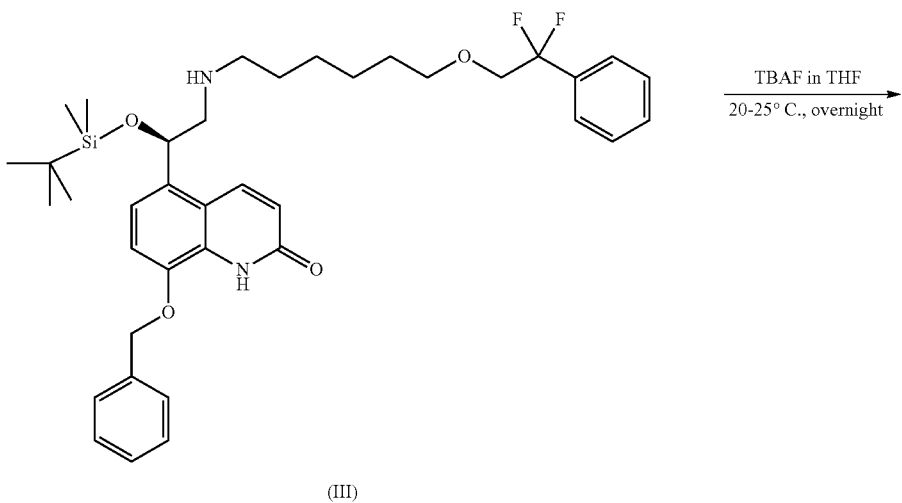

Step c)
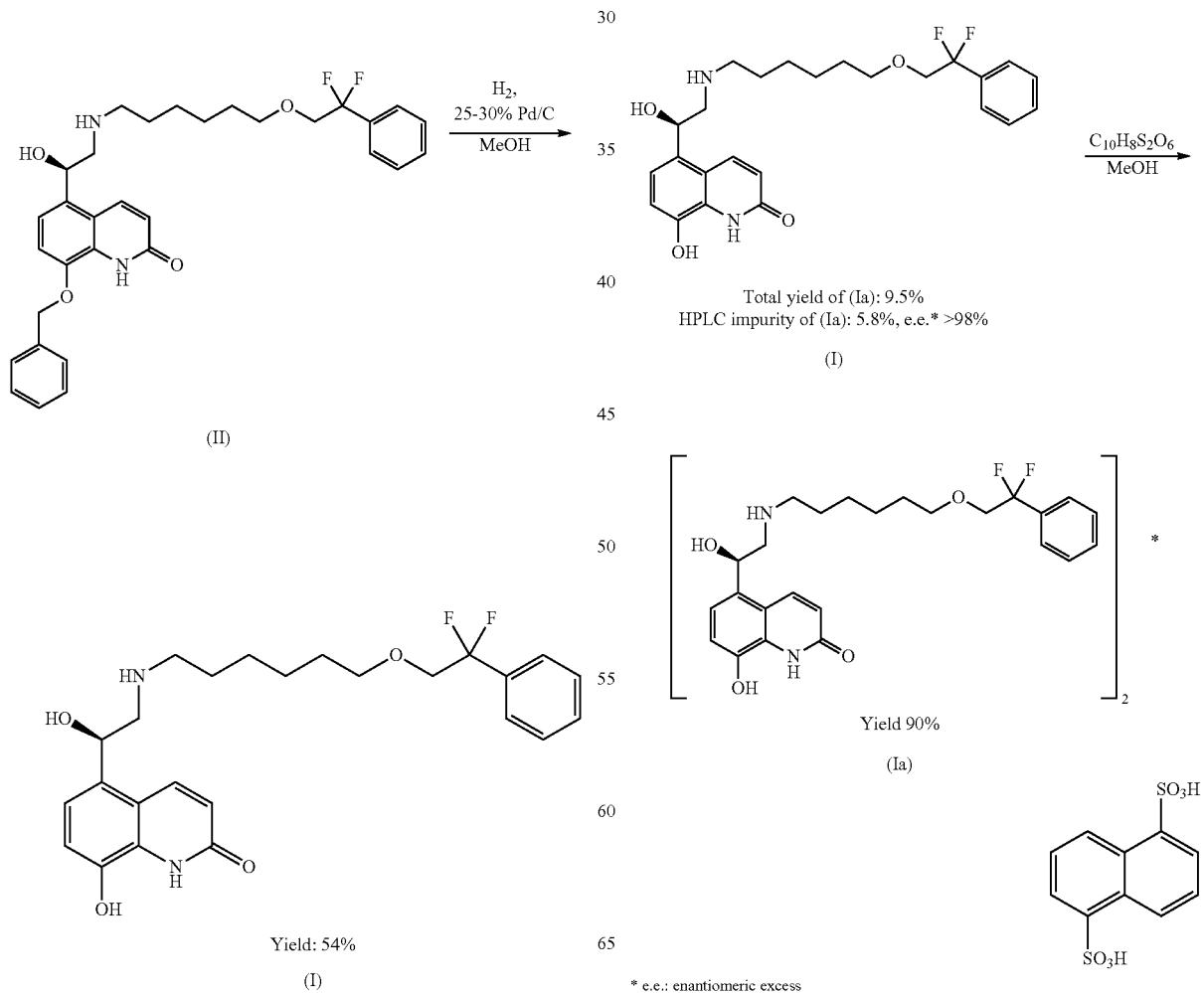
WO 2008095720 A1 discloses a method for preparing the napadisylate salt compound of formula (Ia):
Step d)
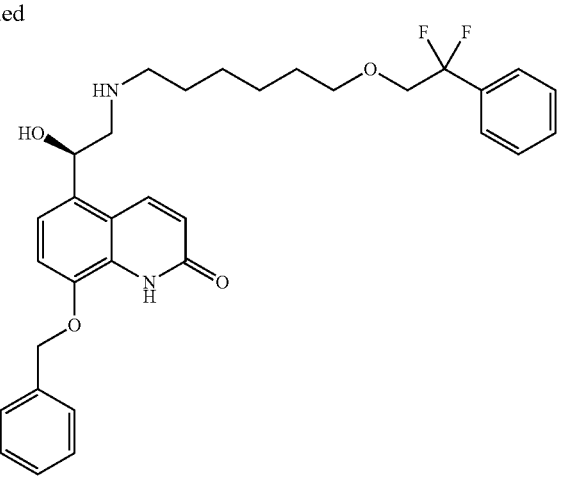
* e.e.: enantiomeric excess As a consequence, in order to prepare a napadisylate salt compound of formula (Ia) from intermediates (V) and (IV), according to the techniques disclosed in the prior art, four reaction steps must be carried out, wherein each intermediate, once obtained, was isolated and purified before being used as a starting material in the following step. The purification steps in the prior art techniques were carried out using conventional purification methods already known in the art such as, for example, solvent extraction or chromatography techniques. The overall yield for preparing the napadisylate compound (Ia) was calculated to be about 9.5% while the level of impurities determined by HPLC analysis was about 5-6%.

It has been surprisingly found that the process for preparing 5-(2-{[6-(2,2-difluoro-2-phenylethoxy)hexyl]amino}-1-hydroxyethyl)-8-hydroxyquinolin-2(1H)-one and its salts can be significantly improved by modifying the reaction conditions, particularly by modifying or even removing purification processes in some steps thus simplifying the numerous reaction steps while increasing the overall yield of the reactions. Moreover, it has been found that by proper selection of solvents, the required product can be obtained with a higher yield and in a more pure form compared with the earlier process.

Accordingly, the present invention provides a process for preparing a 5-(2-{[6-(2,2-difluoro-2-phenylethoxy)hexyl]amino}-1-hydroxyethyl)-8-hydroxyquinolin-2(1H)-one compound of formula (I), or a pharmaceutically acceptable salt thereof,

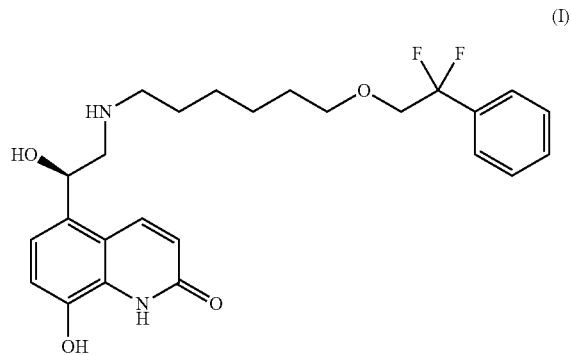 [SMILES: O=c1ccc2c([C@@H](O)CNCCCCCCOCC(F)(F)c3ccccc3)ccc(O)c2[nH]1]

(I)

which process comprises:
a) reacting, in a xylene solvent, a compound of formula (V)

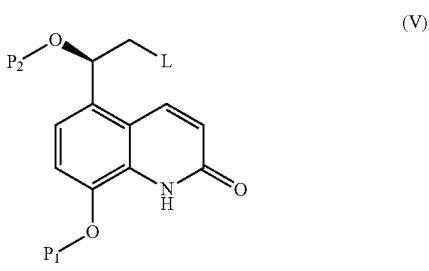

(V)

wherein $P_1$ and $P_2$ represent hydroxy protecting groups and L is a leaving group, with 6-(2,2-difluoro-2-phenylethoxy)hexan-1-amine of formula (IV),

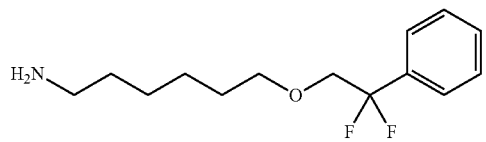

(IV)

to give a compound of formula (III)

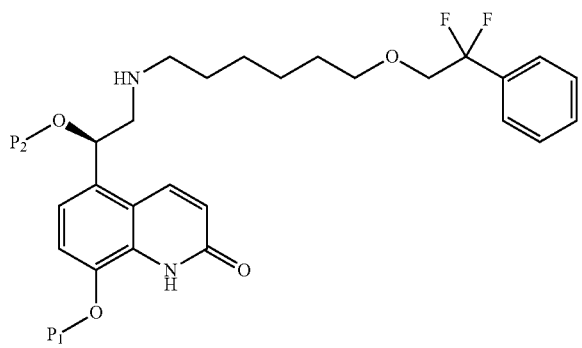

(III)

b) effecting a $P_1$ deprotection step and a $P_2$ deprotection step, to remove the protecting groups $P_1$ and $P_2$ and give a compound of formula (I).

Typically,
(i) the $P_2$ deprotection step is carried out at a temperature ranging from 30-60° C. for up to 8 hours, and/or
(ii) the $P_1$ deprotection step is carried out in the presence of a solvent which is acetic acid or a mixture of acetic acid with an alcohol or with an ester.

Step (a) is conducted in a xylene solvent. In contrast, the corresponding reaction step disclosed in WO 2006/122788 is effected in DMSO. It is a surprising finding of the present invention that the use specifically of a xylene solvent enables a significant improvement in the purity of the compound of the formula (III).

In a preferred embodiment, step (b) above comprises:
effecting said $P_2$ deprotection step on the compound of formula (III) to yield a compound of formula (II),

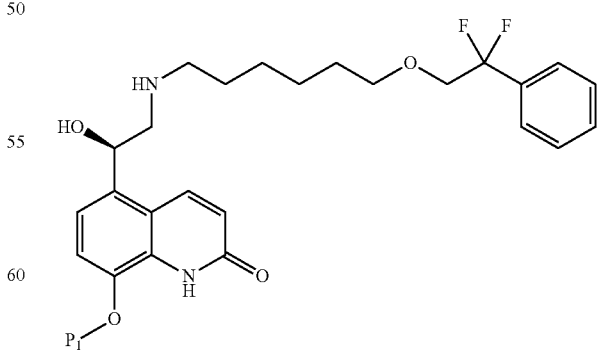

(II)

wherein $P_1$ is as defined above; and
effecting said $P_1$ deprotection step on the compound of formula (II) to give a compound of formula (I),

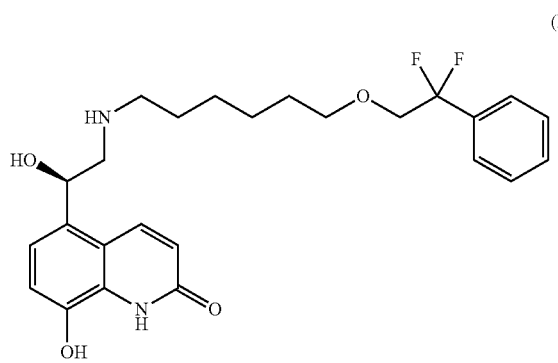
(I)

Thus, in this embodiment, the present invention provides a process for preparing a 5-(2-{[6-(2,2-difluoro-2-phenylethoxy)hexyl]amino}-1-hydroxyethyl)-8-hydroxyquinolin-2(1H)-one compound of formula (I), or a pharmaceutically acceptable salt thereof,

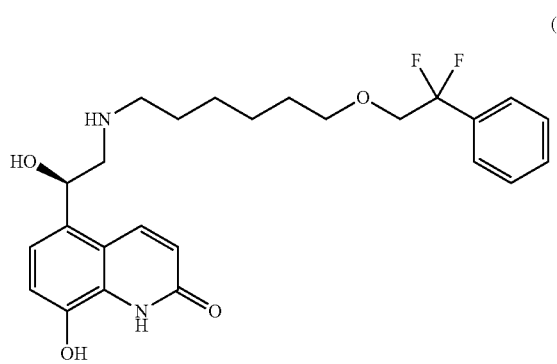
(I)

which process comprises:
a) reacting, in a xylene solvent, a compound of formula (V)

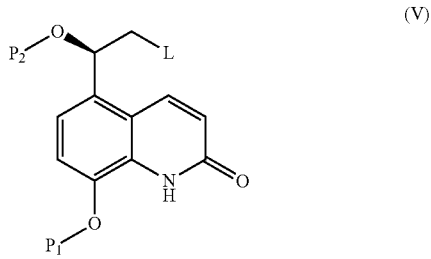
(V)

wherein $P_1$ and $P_2$ represent hydroxy protecting groups and L is a leaving group, with 6-(2,2-difluoro-2-phenylethoxy)hexan-1-amine of formula (IV),

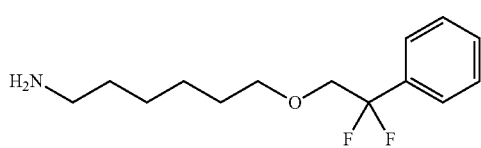
(IV)

to give a compound of formula (III)

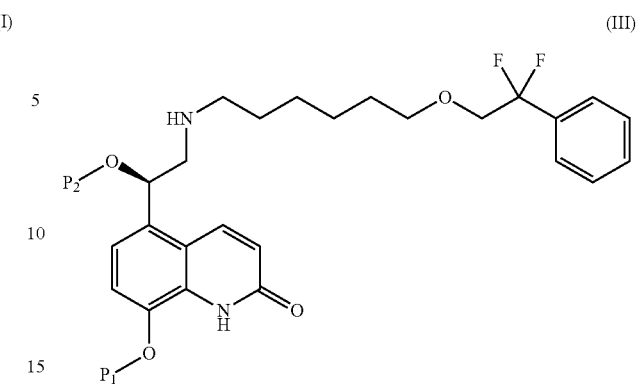
(III)

b) deprotecting the compound of formula (III) to yield a compound of formula (II),

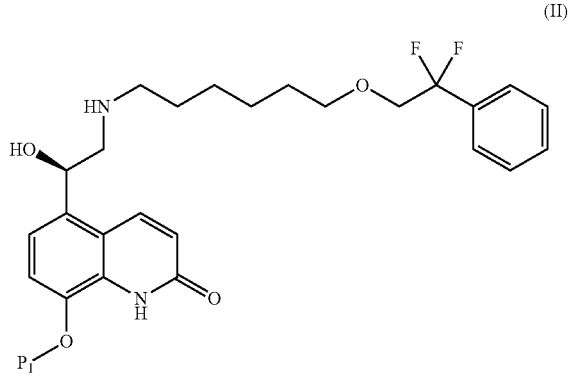
(II)

wherein $P_1$ is as defined above; and c) deprotecting the compound of formula (II) to give a compound of formula M.

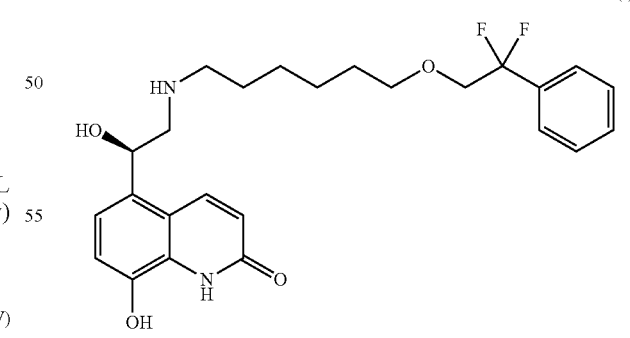
(I)

Typically, in this embodiment:
(i) step b) is carried out at a temperature ranging from 30-60° C. for up to 8 hours, and/or
(ii) step c) is carried out in the presence of a solvent which is acetic acid or a mixture of acetic acid with an alcohol or with an ester.

In a further embodiment, the process of the present invention comprises:

a) reacting, in a xylene solvent, a compound of formula (V)

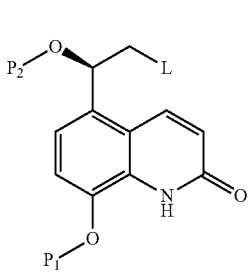
(V)

wherein $P_1$ and $P_2$ represent hydroxy protecting groups and L is a leaving group, with 6-(2,2-difluoro-2-phenylethoxy)hexan-1-amine of formula (IV),

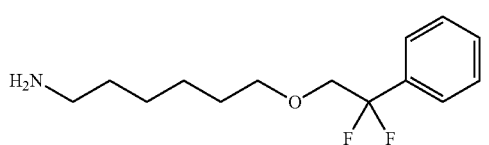
(IV)

to give a compound of formula (III)

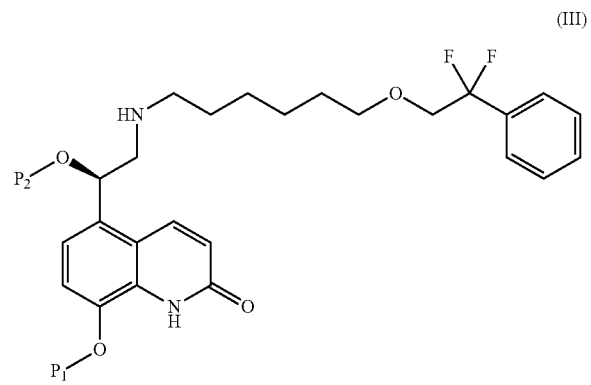
(III)

b) deprotecting the compound of formula (III) to yield a compound of formula (II'),

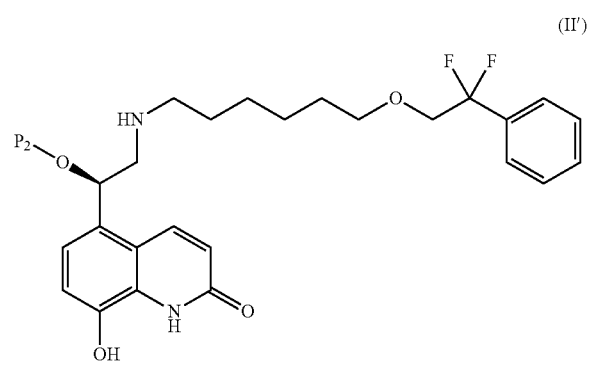
(II')

wherein $P_2$ is as defined above; and c) deprotecting the compound of formula (II') to give a compound of formula (I).

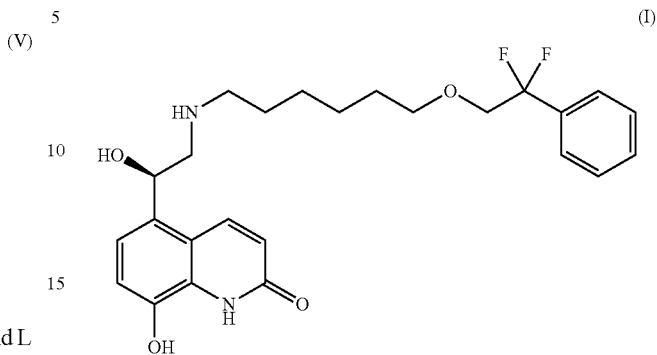
(I)

Typically, in this embodiment:
(i) step b) is carried out in the presence of a solvent which is acetic acid or a mixture of acetic acid with an alcohol or with an ester; and/or
(ii) step c) is carried out at a temperature ranging from 30-60° C. for up to 8 hours. $P_1$ and $P_2$ are hydroxy protecting groups. $P_1$ and $P_2$ may be the same or different. Preferably, they are different. A skilled chemist can easily select suitable hydroxy protecting groups for the $P_1$ and $P_2$ positions. For example, appropriate protecting groups are discussed in T. W. Greene and G. M. Wuts, Protecting Groups in Organic Synthesis, Third Edition, Wiley, New York, 1999, and references cited therein.

Examples of suitable hydroxy protecting groups include alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

Typically $P_1$ is a benzyl group. In this embodiment, the $P_1$ deprotection step is typically effected by hydrogenation, preferably in the presence of a catalyst such as, palladium (II) hydroxide (Pd(OH)$_2$) or palladium (0) (Pd(0)). Preferably, the catalyst is palladium (0) on charcoal.

Typically, in this embodiment, the hydrogenation reaction of the $P_1$ deprotection step is carried out in the presence of catalyst in an amount less than 10%, preferably less than 5% most preferably about 4% by weight with respect of the amount of the reactant used. The use of catalyst in these amounts typically enables a reduction in the level of impurities generated. In particular, it can reduce the formation of the defluoro impurity, i.e. 5-(2-{[6-(2-phenylethoxy)hexyl]amino}-1-hydroxyethyl)-8-hydroxyquinolin-2(1H)-one. It can also reduce the formation of dihydroquinoline impurities.

Typically, $P_2$ is a tert-butyldimethylsilyl moiety. In this embodiment, the $P_2$ deprotection step is typically effected by reaction with tetra-n-butyl ammonium fluoride, trihydrate (TBAF) preferably in a solvent such as tetrahydrofuran (THF), or with hydrogen chloride in a solvent selected from ethers, esters and alcohols. Preferably, in this embodiment, the $P_2$ deprotection step is carried out with hydrogen chloride in a solvent selected from diethyl ether, tert-butylmethylether (TBME), ethanol and isopropylacetate.

Alternatively, in this embodiment, the $P_2$ deprotection step is preferably carried out with TBAF in tetrahydrofuran (THF) or 2-methyltetrahydrofuran, preferably in THF.

Alternatively, in this embodiment the $P_2$ deprotection step is preferably carried out with naphthalene-1,5-disulfonic acid in tetrahydrofuran (THF).

L is a leaving group. A skilled chemist would easily be able to select appropriate leaving groups for the L position. Examples of suitable leaving groups include halogen atoms, mesylate groups (—O—S(O)$_2$—CH$_3$) and triflate (—OS(O)$_2$—CF$_3$) groups.

Preferably, L is halogen atom. More preferably, L is a bromine atom.

Typically, the solvent used in step (a) is substantially free of DMSO. More preferably, it is substantially free of DMSO and dioxane.

Use of the xylene solvent detailed above in step (a) enables an overall improvement in purity and/or yield, as compared with analogous processes in which step (a) is conducted in solvents such as DMSO.

In another embodiment of the present invention, the $P_2$ deprotection step is carried out at a temperature ranging from 40-50° C. for a time period not exceeding 6 hours, preferably not longer than 4 hours, more preferably not longer than 2 hours, most preferably up to one hour. The reduction in the reaction time for the $P_2$ deprotection step enables a surprising decrease in the formation of undesired by-products.

In a still another embodiment, the hydrogenation of the $P_2$ deprotection step is optionally carried out in the presence of tetrabutylammonium fluoride in an amount of about 0.3-0.9 g of TBAF per gram of reactant. Typically, the reactant is the compound of formula (II).

In another embodiment of the present invention, the compound obtained from the $P_2$ deprotection step is purified by crystallization. Typically, crystallization is effected with 1,5-naphthalenedisulphonic acid in alcohol, preferably ethanol. Purification of the compound obtained from the $P_2$ deprotection step by crystallization, rather than by chromatography, enables an improvement in purity and/or yield. Preferably, in this embodiment, the $P_2$ deprotection step is effected before the $P_1$ deprotection step, and the compound obtained from the $P_2$ deprotection step is therefore a compound of formula (II).

In a preferred embodiment of the invention, the $P_1$ deprotection step is carried out in the presence of a solvent which is acetic acid or a mixture of acetic acid with an alcohol or with an ester. Preferably, in this embodiment, the solvent is acetic acid alone or a mixture of acetic acid/methanol (1:1), more preferably acetic acid/methanol (1:1).

Typically, said solvent contains less than 5% (v/v), preferably less than 3%, more preferably less than 1%, of any liquid other than acetic acid, an alcohol and an ester, preferably of any liquid other than acetic acid and methanol.

In a preferred embodiment of the invention, a pharmaceutically acceptable salt of a compound of formula (I) is prepared. Preferably said salt is a napadisylate salt or a mesylate salt.

The napadisylate salts are typically those described in WO 2008/095720. Preferably the napadisylate salt is a heminapadisylate salt or a mononapadisylate salt. A mononapadisylate salt typically contains between about 0.8 and 1.2 molar equivalents of naphthalene-1,5-disulfonic acid per molar equivalent of the free base, more typically about 1.0 molar equivalents of naphthalene-1,5-disulfonic acid per molar equivalent of the free base. A heminapadisylate salt typically contains between about 0.35 and 0.65 molar equivalents of naphthalene-1,5-disulfonic acid per molar equivalent of the free base, more typically about 0.5 molar equivalents of napthalene-1,5-disulfonic acid per molar equivalent of the free base.

The present invention is also directed to 5-(2-{[6-(2,2-difluoro-2-phenylethoxy)hexyl]amino}-1-hydroxyethyl)-8-hydroxyquinolin-2(1H)-one, or a pharmaceutically acceptable salt thereof, obtainable by the process of the invention. Preferably, the present invention is directed to a napadisylate salt or mesylate salt of 5-(2-{[6-(2,2-difluoro-2-phenylethoxy)hexyl]amino}-1-hydroxyethyl)-8-hydroxyquinolin-2(1H)-one obtainable by the process of the invention. More preferably, the salt is the napadisylate salt.

The above molar ratios can be determined by standard techniques, for example $^1$H NMR, elemental analysis and HPLC methods.

When a napadisylate salt of a compound of formula (I) is prepared, typically, following step (b), naphthalene-1,5-disulfonic acid is added without isolating the 5-[2-{[6-(2,2-difluoro-2-phenyl ethoxy)hexyl]amino}-1-hydroxyethyl)-8-hydroxyquinolin-2(1H)-one of formula (I). Preparing the final product in a one-pot reaction in this way without isolating the free base can improve purity and/or yield. Further, such a one-pot reaction is also advantageous because it enables greater process efficacy.

In a preferred embodiment of the invention, step (b) and, if required, the subsequent salification step are each conducted without purifying the intermediate obtained from the previous reaction step.

The compounds of formula (V) can be obtained by known methods, or by analogy with known methods. For example, the compound in which $P_1$ is benzyl and $P_2$ is TBS can be obtained by the synthetic methods described in US2004059116 (Example 9C), WO2004/011416 (Example 2) and WO2004/016578 (Example 1ii).

6-(2,2-Difluoro-2-phenylethoxy)hexan-1-amine (IV) is obtained by synthetic method described in WO 2006122788 A1 (Intermediate 9).

The reagents and solvents used in the present invention are commercially available, for example from Aldrich Chemical Company, Inc. or Fluka Chemie GmbH.

The Preferred Conditions for the Process of Step (a) are the Following:

To a solution of 10.30-11.30 g (40-44 mmol) of 6-(2,2-Difluoro-2-phenylethoxy)hexan-1-amine (IV) in 15-25 ml of a xylene solvent, is added 19.9 g (40 mmol) of (R)-8-(Benzyloxy)-5-(2-bromo-1-(tert-butyldimethylsilyloxy)ethyl)quinolin-2(1H)-one (V) and 9-12 g of sodium bicarbonate or 15-20 g of potassium carbonate. The reaction mixture is heated to reflux during 4-6 h. After cooling down to room temperature, the precipitated inorganic salts are filtered and washed with 80-120 ml of xylene. The solvent is removed thus obtaining an oily residue which is used in the next step without further purification The Preferred Conditions for the $P_2$ Deprotection Step are the Following:

The oily residue obtained from the previous step is dissolved in 300-350 ml of THF. Then 20-25 g of TBAF is added to the reaction medium. The reaction mixture is stirred during 1-2 hour at 40-50° C. After cooling down to room temperature, the solvent is removed under vacuum. A total 250-300 ml of water/organic solvent (1:1) is added to the residue. The organic layer is separated and the aqueous layer is extracted twice with the organic solvent (2×20-30 ml). The organic layers are combined and concentrated under vacuum to remove the solvent. The preferred organic solvents used in the extraction work-up are toluene, dichloromethane, isopropyl acetate or Methyl-Isobutyl-Ketone (MIK), more preferably toluene, isopropyl acetate or dichloromethane, being most preferably isopropyl acetate or dichloromethane. In an alternative process, the residue obtained, once the reaction solvent (THF) has been removed, may be used directly in the next crystallization purification without aqueous extraction work-up The residue is purified by crystallization with 8-9 g of 1,5-naftalenedisulphonic acid tetrahydrate in 300-400 ml of ethanol. The product obtained is filtered and washed with 50-70 ml of ethanol. The wet cake obtained is treated with in 250-260 ml of methanol/dichloromethane (1:2), methanol/isopropyl acetate (1:2) or methanol/toluene (1:2). To this suspension is added a solution of 3.5-4 g of NaOH in 170-190 ml of water. The reaction mixture is stirred at 20-30° C. during 40-50 minutes. The organic phase is separated and the solvent is removed under vacuum.

The Preferred Conditions for the Process of the $P_1$ Deprotection Step are the Following Intermediate (H) is dissolved in a total volume of 160-170 ml of acetic acid/alcohol (1:1), preferably acetic acid/methanol. 1-1.5 g of 10% Pd/C, 50% water is added to the solution. Then, about 5-15 g of TBAF is optionally added to the solution. After several purges of nitrogen, the reaction mixture in hydrogenated at a temperature of 20-30° C. at less than 4 bars, preferably at 1-2 bars, during 6-8 h. The catalyst is then filtered and washed with 190-200 ml of methanol. About 200-250 ml of acetic acid is added to the filtrate and a solution of 6-6.5 g of 1,5-naphtalenedisulfonic acid tetrahydrate in 50-70 ml of methanol/acetic acid (1:1) is added to this filtrate. The mixture is heated to reflux for 30 minutes. After cooling down to room temperature, the product is filtered and washed with 25-30 ml of methanol. The product obtained may optionally be purified by slurry with methanol in hot conditions such as at a boiling temperature of methanol. The final product (Ia) is dried under vacuum at 50° C.

The method of synthesis described in the present invention will be further illustrated by the following examples. The examples are given by the way of illustration only and are not to be construed as limiting.

The structures of the prepared compounds were confirmed by $^1$H-NMR and MS. NMR were recorded using a Varian Gemini-200 NMR spectrometer operating at frequency of 200 or 300 MHz. Tetramethyl silane was used as a reference and samples were solved in deuterated dimethylsulphoxide (DMSO-$d_6$) or deuterated chloroform (CDCl$_3$).

Their purity was determined by HPLC, in Alliance 2795 Waters instrument equipped with diode array detector (DAD) and ZMD or ZQ mass detector (electrospray ionization). HPLC method used a Symmetry C18 column (3.5 21×100 mm) and mobile phase was composed by two phases: Phase A: Buffered (Formic acid/ammonia) aqueous solution at pH: 3. Phase B: 50.50 mixture acetonitrile/methanol with ammonium formate. Gradient was from 0% to 95% of phase B in 10 minutes.

Preparative HPLC-MS experiments were performed on a Gilson instrument equipped with a binary pump (Gilson piston pump 321); a vacuum degasser (Gilson 864); an injector-fraction collector (Gilson liquid handler 215); two injection modules, analytical and preparative (Gilson 819); a valve (Gilson Valvemate 7000); a 1/1000 splitter (Acurate by LC Packings); a make-up pump (Gilson 307); a diode array detector (Gilson 170) and a MS detector (a Thermoquest Finnigan aQa, a quadrupole mass spectrometer with ES and APCI ionisation modes). The HPLC-MS instrument was controlled by an IBM PC.

EXPERIMENTAL SECTION

Comparative Example I

According to WO 2006122788 and WO 2008095720

Intermediate III. 8-(benzyloxy)-5-((1R)-1-{[tert-butyl(dimethyl)silyl]oxy}-2-{[6-(2,2-difluoro-2-phenylethoxy)hexyl]amino}ethyl)quinolin-2(1H)-one To a solution of (8-(benzyloxy)-5-((1R)-2-bromo-1-{[tert-butyl(dimethyl)silyl]oxy}ethyl)quinolin-2(1H)-one (V) (4.80 g, 9.83 mmol) and 6-(2,2-Difluoro-2-phenylethoxy) hexyl]amine (IV) (3.04 g, 11.8 mmol) in dimethylsulfoxide (13.5 mL) was added sodium bicarbonate (2.49 g, 29.4 mmol) and sodium iodide (2.22 g, 14.8 mmol). The mixture was heated at 140° C. for 2 hours. After cooling, the reaction was diluted with water (40 mL) and extracted with diethyl ether (2×20 mL). The combined organic extracts were washed with water (2×10 mL) and brine (20 mL), dried (Na$_2$SO$_4$), and the solvent removed under reduced pressure. The title compound was obtained (6.40 g, 98%) as oil.

Intermediate (II). 8-(benzyloxy)-5-((1R)-2-{[6-(2,2-difluoro-2-phenylethoxy)hexyl]amino}-1-hydroxy-ethyl)quinolin-2(1H)-one To a solution of Intermediate (III) (6.4 g, 9.63 mmol) in tetrahydrofuran (60 mL) was added TBAF (5.02 g, 19.26 mmol). The mixture was stirred at room temperature overnight. The solvent was removed under reduced pressure. Purification by column chromatography using methylene chloride/methanol (from 95:5 to 85:15) as eluent gave 8-(benzyloxy)-5-((1R)-2-{[6-(2,2-difluoro-2-phenylethoxy) hexyl]amino}-1-hydroxy ethy)quinolin-2(1H)-one (II) (1.1 g, 20%) as oil.

5-((1R)-2-{[6-(2,2-difluoro-2-phenylethoxy)hexyl] amino}-1-hydroxyethyl)-8-hydroxyquinolin-2(1H)-one (I)

To Intermediate (II) (1.10 g, 2.0 mmol) in methanol (50 mL) was added 20% palladium on charcoal (300 mg). The mixture was hydrogenated at 2 bars for 3 hours. The catalyst was filtered through Celite and the solvent concentrated. The resulting oil was purified by column chromatography with silica gel eluting with methylene chloride/methanol (95:5) to give the title compound (0.50 g, 54%) as oil.

5-((1R)-2-{[6-(2,2-difluoro-2-phenylethoxy)hexyl] amino}-1-hydroxyethyl)-8-hydroxyquinolin-2(1H)-one napadisylate salt (Ia)

5-((1R)-2-{[6-(2,2-difluoro-2-phenylethoxy)hexyl] amino}-1-hydroxyethyl)-8-hydroxyquinolin-2(1H)-one (6.63 g; 14.4 mmol) was dissolved in 134 ml of methanol to form a 1,075 M solution which is heated to approximately 50° C. Then, 7.74 mmol of naphthalene-1,5-disulfonic acid, tetrahydrate were added to the heated solution. The mixture was then stirred for 30 minutes at reflux temperature and then cooled down to 20/25° C. and stirred at this temperature for 1 additional hour. The precipitate formed was isolated by filtration, washed with methanol and dried in vacuum at 50° C. (15.67 g, 90%)

Example II

According to the Present Invention

Intermediate III. 8-(benzyloxy)-5-((1R)-1-{[tert-butyl(dimethyl)silyl]oxy}-2-{[6-(2,2-difluoro-2-phenylethoxy)hexyl]amino}ethyl)quinolin-2(1H)-one To a solution of [6-(2,2-Difluoro-2-phenylethoxy)hexyl] amine (IV) (11.0 g, 42.8 mmol) in xylene (20 mL) were added (8-(benzyloxy)-5-((1R)-2-bromo-1-{[tert-butyl(dimethyl)silyl]oxy}ethyl)quinolin-2(1H)-one (V) (19.9 g, 40.7 mmol) and sodium bicarbonate (10.4 g, 123 mmol). The mixture was heated at reflux for 6 hours. After cooling down to room temperature, additional xylene (176 ml) was added to the reaction mixture and the precipitated inorganic salts were filtrated and washed with xylene (100 ml). The obtained filtrate was concentrated under vacuum to remove the solvent, thus yielding an oily residue (Intermediate (III)) which was used in the next step without purification.

Intermediate (II). 8-(benzyloxy)-5-((1R)-2-{[6-(2,2-difluoro-2-phenylethoxy)hexyl]amino}-1-hydroxyethyl)quinolin-2(1H)-one Intermediate (III) was dissolved in tetrahydrofuran (330 mL). Then TBAF (23.3 g, 73 mmol) was added to this solution. The mixture was stirred at 45° C. during 1 hour. After cooling down to room temperature, the solvent was removed under vacuum and the resulting residue was optionally extracted with 266 ml of a mixture water/dichloromethane (1:1). The organic layers were recovered and then removed under vacuum. Then 352 ml of ethanol 96% was added and the mixture was heated to 50-60° C. At this temperature, a solution of 8.5 g of 1,5-naphtalenedisulphonic acid tetrahydrate in 35 ml of ethanol 96% is added during 1 hour. The system of addition was washed with 29 ml of ethanol 96% which is added to the reaction mixture. The reaction mixture is stirred at reflux during 30 minutes and then cooled down to room temperature. The product is filtered and washed with 60 ml of ethanol. The wet cake product is treated with 252 ml of methanol/dichloromethane (1:2). Then a solution of 3.6 g of NaOH in 116 ml of water is added and the reaction mixture is stirred at 20-25° C. during 45 minutes. The aqueous layer is separated and extracted with dichloromethane (3×42 ml). The organic phases are recovered and stirred together with a solution of 4.2 g of NaCl in 168 ml of water. The organic phase is separated and the solvent is removed under vacuum, thus yielding 8-(benzyloxy)-5-((1R)-2-{[6-(2,2-difluoro-2-phenylethoxy)hexyl]amino}-1-hydroxyethy)quinolin-2(1H)-one (II) (16.8 g, 75%) as oil.

5-((1R)-2-{[6-(2,2-difluoro-2-phenylethoxy)hexyl]amino}-1-hydroxyethyl)-8-hydroxyquinolin-2(1H)-one napadisylate salt (Ia)

To a solution of Intermediate (II) (16.8 g, 30.5 mmol) in a mixture of methanol (69 mL) and acetic acid (77 ml) was added a suspension of 10% palladium on charcoal, 50% water, (1.33 g) in a mixture of methanol (15 ml) and acetic acid (7 ml). The mixture was hydrogenated at 1-2 bars for 8 hours. The catalyst was filtered through Celite and washed with methanol (193 ml). Acetic acid (220 ml) was added to this filtrate. Then a solution of 1,5-naphtalenedisulphonic acid, tetrahydrate (6.33 g) in a mixture of methanol (54 ml) and acetic acid (27 ml) was added slowly to the filtrate. The reaction mixture is heated at reflux during 30 minutes, and then cooled down to room temperature. The precipitated was filtered and washed with methanol (27 ml). The wet crude product is dissolved in methanol (800 ml) and heated to reflux during 30 min. The product is filtered and washed with additional methanol (34 ml). The solid thus obtained is dried under vacuum at 50° C., thus yielding 5-((1R)-2-{[6-(2,2-difluoro-2-phenylethoxy)hexyl]amino}-1-hydroxyethyl)-8-hydroxyquinolin-2(1H)-one napadisylate salt (14.9 g, 81%).

The overall yield of 5-((1R)-2-{[6-(2,2-difluoro-2-phenylethoxy)hexyl]amino}-1-hydroxyethyl)-8-hydroxyquinolin-2(1H)-one napadisylate salt (Ia) is Calculated to be about 60.7% (75%×81%) and the purity thereof is HPLC imp=1.5%, e:e. >98%.

TABLE 1 comparative results

| Reaction step | Comparative Example | Example of the invention |
| --- | --- | --- |
| Step (a) | Product obtained included 39% of impurities | Product obtained included 7% of impurities |
| Step (b)* | Yield: 20% | Yield: 75% |
| Step (c)** | Yield: 54% | Yield: 81% |
| Step (d) | Yield: 90% | |
| Total Yield | 9.5% | 60.75% |
| Impurities of final product (Ia) | 5.8% | 1.5% |

*$P_2$ deprotection step
**$P_1$ deprotection step

As it can be observed from Table 1, use of a xylene solvent in step (a) significantly reduced the amount of impurities in the intermediate of formula (III). Further, the overall yield of 5-((1R)-2-{[6-(2,2-difluoro-2-phenylethoxy)-hexyl]amino}-1-hydroxyethyl)-8-hydroxyquinolin-2(1H)-one napadisylate salt has drastically increased while the impurity has decreased at a lower level when compared with the comparative example. This is achieved by modifying some purification techniques, thus simplifying the reaction steps and reducing the quantity of different reagents.

The invention claimed is:

1. A process for preparing a compound of formula (I)

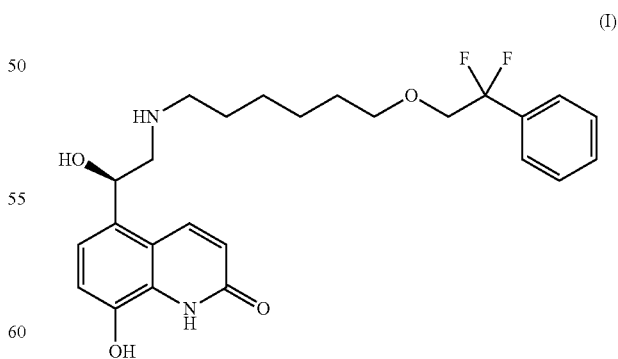

(I)

or a pharmaceutically acceptable salt thereof,
the process comprising:
a) reacting, in a xylene solvent, a compound of formula (V)

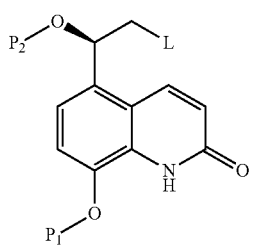

wherein $P_1$ and $P_2$ represent hydroxy protecting groups, which are the same or different, and L is a leaving group, with 6-(2,2-difluoro-2-phenylethoxy)hexan-1-amine of formula (IV),

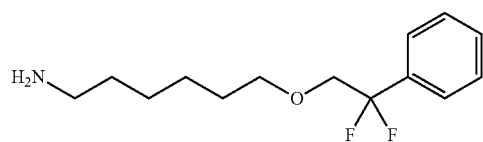

to give a compound of formula (III)

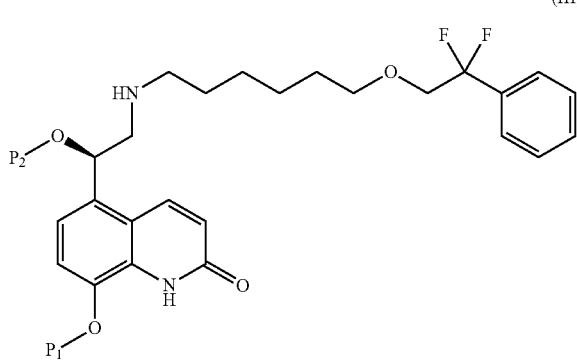

b) effecting a $P_1$ deprotection step and a $P_2$ deprotection step, to remove the protecting groups $P_1$ and $P_2$ and give a compound of formula (I); and c) optionally preparing a pharmaceutically acceptable salt of a compound of formula (I).

2. The process according to claim 1, wherein at least one of the following conditions is met:

(i) the $P_2$ deprotection step is carried out at a temperature ranging from 30-60° C. for up to 8 hours, and (ii) the $P_1$ deprotection step is carried out in the presence of a solvent selected from acetic acid, a mixture of acetic acid with an alcohol, and a mixture of acetic acid with an ester.

3. The process according to claim 1, wherein step (b) comprises:

effecting said $P_2$ deprotection step on the compound of formula (III) to yield a compound of formula (II),

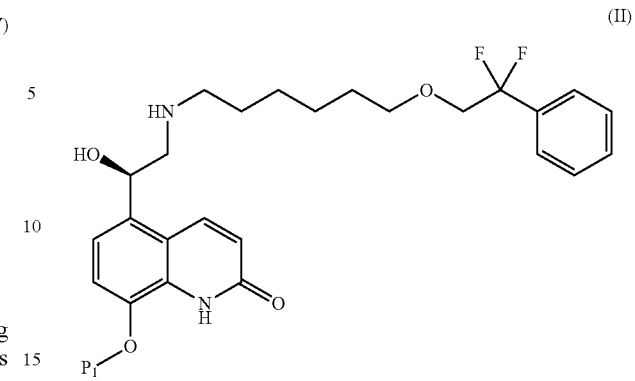

and effecting said $P_1$ deprotection step on the compound of formula (II) to give a compound of formula (I),

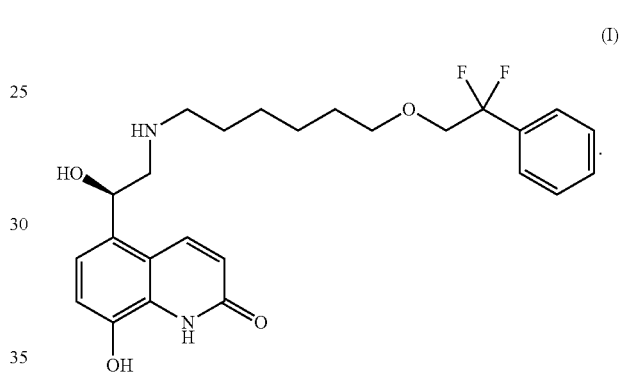

4. The process according to claim 1, wherein at least one of the following conditions is met:

(a) $P_1$ is a benzyl group and the $P_1$ deprotection step is effected by hydrogenation, and (b) $P_2$ is a tert-butyldimethylsilyl group and the $P_2$ deprotection step is effected by reaction with tetra-n-butyl ammonium fluoride trihydrate or with hydrogen chloride.

5. The process according to claim 1, wherein L is bromine.

6. The process according to claim 1, wherein the $P_2$ deprotection step is carried out with tetra-n-butyl ammonium fluoride trihydrate in tetrahydrofuran.

7. The process according to claim 1, wherein the $P_2$ deprotection step is carried out at a temperature ranging from 40-50° C. for a time period of 6 hours or less.

8. The process according to claim 7, wherein the time period is 4 hours or less.

9. The process according to claim 1, wherein the compound prepared is selected from a heminapadisylate salt of the compound of formula (I) and a mesylate salt of the compound of formula (I).

10. The process according to claim 9, wherein, following step (b), napthalen-1,5-disulfonic acid is added without isolating the 5-[2-{[6-(2,2-difluoro-2-phenylethoxy)hexyl]amino}-1-hydroxyethyl)-8-hydroxyquinolin-2(1H)-one compound of formula (I).

11. The process according to claim 3, wherein the compound of formula (II) obtained from the $P_2$ deprotection step is purified by crystallization with naphtalen-1,5-disulphonic acid tetrahydrate in ethanol.

12. The process according to claim 1, wherein $P_1$ is benzyl and the $P_1$ deprotection step is effected by hydrogenation in the presence of palladium on charcoal catalyst in an amount less than 10% (w/w) with respect to the amount of the compound of formula (II).

13. The process according to claim 12, wherein the amount of the catalyst used is less than 5% by weight with respect to the amount of the compound of formula (II).

14. The process according to claim 1, wherein, the $P_1$ deprotection step is carried out in the presence of a solvent selected from acetic acid and a mixture of methanol/acetic acid (1:1).

15. The process according to claim 14, wherein the solvent is methanol/acetic acid (1:1).

16. The process according to claim 1, wherein
   the $P_2$ deprotection step is carried out at a temperature ranging from 30-60° C. for up to 8 hours, and
   the $P_1$ deprotection step is carried out in the presence of a solvent selected from acetic acid, a mixture of acetic acid with an alcohol, and a mixture of acetic acid with an ester.

* * * * *